US012148529B2

(12) United States Patent
Levin et al.

(10) Patent No.: US 12,148,529 B2
(45) Date of Patent: Nov. 19, 2024

(54) E-TRIAGE: AN ELECTRONIC EMERGENCY TRIAGE SYSTEM

(71) Applicant: THE JOHNS HOPKINS UNIVERSITY, Baltimore, MD (US)

(72) Inventors: Scott R. Levin, Baltimore, MD (US); Thomas Kirsch, Baltimore, MD (US); Matthew Toerper, Cockeysville, MD (US); Gabor D. Kelen, Baltimore, MD (US); Andrea Dugas, Silver Spring, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 1 day.

(21) Appl. No.: 16/544,016

(22) Filed: Aug. 19, 2019

(65) Prior Publication Data

US 2020/0005188 A1    Jan. 2, 2020

Related U.S. Application Data

(63) Continuation of application No. 15/435,746, filed on Feb. 17, 2017, now abandoned.

(60) Provisional application No. 62/296,753, filed on Feb. 18, 2016.

(51) Int. Cl.
| | |
|---|---|
| *G16H 50/20* | (2018.01) |
| *G06N 5/01* | (2023.01) |
| *G06N 20/00* | (2019.01) |
| *G06N 20/20* | (2019.01) |
| *G16H 10/60* | (2018.01) |
| *G16H 50/30* | (2018.01) |

(52) U.S. Cl.
CPC ............. *G16H 50/20* (2018.01); *G06N 5/01* (2023.01); *G06N 20/00* (2019.01); *G06N 20/20* (2019.01); *G16H 10/60* (2018.01); *G16H 50/30* (2018.01)

(58) Field of Classification Search
CPC ............................ G16H 10/60; G16H 50/30
See application file for complete search history.

(56) References Cited

U.S. PATENT DOCUMENTS

| 7,716,070 | B2 | 5/2010 | Glimp et al. | |
|---|---|---|---|---|
| 2004/0176980 | A1* | 9/2004 | Bulitta | G16H 40/20 |
| | | | | 705/2 |
| 2005/0197544 | A1 | 9/2005 | Bernstein | |
| 2006/0122863 | A1* | 6/2006 | Gottesman | G06Q 50/22 |
| | | | | 705/2 |

(Continued)

*Primary Examiner* — Rajesh Khattar
*Assistant Examiner* — Steven G. S. Sanghera
(74) *Attorney, Agent, or Firm* — MH2 Technology Law Group LLP (57) ABSTRACT

An embodiment in accordance with the present invention provides a system that uses simple standardized patient information routinely collected at triage to distribute patients amongst triage levels based on critical and time-sensitive outcomes. The present invention estimates the probability of electronic medical record (EMR) recorded events for patients at triage. Predictions are made for patients based upon clinical information routinely collected at triage which include demographics (age and gender), vital signs (temperature, heart rate, systolic blood pressure, respiratory rate, and oxygen saturation), complaint(s), medical/surgical history, chronic conditions, and mode of arrival. Vital signs are categorized as normal or gradations of abnormal.

24 Claims, 3 Drawing Sheets

(56) References Cited

U.S. PATENT DOCUMENTS

| | | | | |
|---|---|---|---|---|
| 2008/0172214 A1* | 7/2008 | Col | G16H 50/50 | 703/11 |
| 2009/0318775 A1* | 12/2009 | Michelson | G16H 50/50 | 600/300 |
| 2011/0054946 A1 | 3/2011 | Coulter et al. | | |
| 2011/0105852 A1* | 5/2011 | Morris | G06Q 10/10 | 600/300 |
| 2011/0224565 A1* | 9/2011 | Ong | A61B 5/318 | 600/509 |
| 2013/0054264 A1* | 2/2013 | Baronov | G16H 40/63 | 705/2 |
| 2013/0110550 A1* | 5/2013 | Upadhyayula | G16H 50/20 | 705/3 |
| 2013/0317850 A1* | 11/2013 | Bene | G16H 20/40 | 705/3 |
| 2014/0046682 A1* | 2/2014 | Soto | G16H 50/30 | 705/2 |
| 2014/0052465 A1* | 2/2014 | Madan | G16H 40/63 | 705/2 |
| 2014/0052475 A1* | 2/2014 | Madan | G16H 40/63 | 705/3 |
| 2014/0058738 A1* | 2/2014 | Yeskel | G16Z 99/00 | 705/2 |
| 2014/0058755 A1* | 2/2014 | Macoviak | G16H 10/60 | 705/3 |
| 2014/0081092 A1* | 3/2014 | McNair | A61B 5/746 | 600/301 |
| 2014/0135588 A1* | 5/2014 | Al-Ali | G16Z 99/00 | 600/300 |
| 2014/0379363 A1* | 12/2014 | Hart | G16H 50/30 | 705/2 |
| 2015/0025329 A1* | 1/2015 | Amarasingham | G16H 40/63 | 600/301 |
| 2015/0269311 A1* | 9/2015 | Ruddock | G01N 33/57484 | 435/7.92 |
| 2015/0302155 A1* | 10/2015 | Rajan | G16H 50/30 | 702/19 |
| 2016/0012192 A1* | 1/2016 | Radhakrishnan | G16H 40/67 | 706/12 |
| 2016/0029890 A1* | 2/2016 | Stump | A61B 5/0022 | 600/301 |
| 2016/0151603 A1* | 6/2016 | Shouldice | G16H 20/30 | 600/26 |
| 2017/0140114 A1* | 5/2017 | Are | G16H 50/20 | |
| 2018/0075207 A1* | 3/2018 | Schmidt | G16H 50/20 | |
| 2021/0142915 A1* | 5/2021 | Haber | G16H 50/30 | |

* cited by examiner

E-TRIAGE: AN ELECTRONIC EMERGENCY TRIAGE SYSTEM

CROSS REFERENCE TO RELATED APPLICATIONS

This application is a Continuation of U.S. patent application Ser. No. 15/435,746, filed Feb. 17, 2017 which claims the benefit of U.S. Provisional Patent Application No. 62/296,753 filed Feb. 18, 2016, the content of each of the aforementioned applications is herein incorporated by reference in their entirety.

GOVERNMENT SPONSORSHIP

This invention was made with government support under Agency for Healthcare Research in Quality (AHRQ) R21 HS23641-01A1 and 2010-ST-061-PA0001 awarded by the Department of Homeland Security and the National Center for the Study of Preparedness and Catastrophic Even Response. The government has certain rights in the invention.

FIELD OF THE INVENTION

The present invention relates generally to hospital resource management and patient safety. More particularly, the present invention relates to emergency department management software to support objective, risk-based triage evaluation.

BACKGROUND OF THE INVENTION

Increasing patient visits and decreasing capacity due to closing facilities has driven crowded emergency departments (ED) to a breaking point. As ED patient volumes rise, without a corresponding increase in resources, an increasing number of patients must wait to receive medical evaluation and treatment. Thus, to effectively manage large volumes of patients, ED staff must quickly distinguish patients with critical and time-sensitive conditions from those with less urgent needs. Though patients at the extremes of acuity may be easy to identify, the clinical courses of the majority of patients are not obvious. Under-triaged patients potentially suffer otherwise avoidable deterioration, morbidity, and mortality. Over-triaged patients consume limited resources that may be of greater benefit to those with a higher acuity illness. Given the heightened levels of demand for ED services, an accurate triage system is required to provide safe and optimal patient care.

Further, the growing numbers of patients using the ED for non-emergency care has spurred EDs to use triage to stream patients to specific service lines (often separate care areas) based on acute risk and projected resource needs. For example, an increasing number of EDs employ "fast-tracks" to provide non-urgent care for patients to receive limited evaluation and treatment. Safely identifying these patients at presentation is needed to decrease low-acuity patient waiting and prevent ED resource over-utilization, which plagues this costly care setting. To place in context, it has been estimated that between 13% and 56% of ED visits are for non-urgent conditions representing between $24 and $38 billion in wasteful healthcare spending annually.

Although triage has been a long-standing principle in emergency medicine, standardized triage tools are relatively new. Countries such as Canada, Australia, and the United Kingdom have created their own triage instruments; similarly, in the United States, 72% of ED patient visits are assessed using the Emergency Severity Index (ESI). The ESI is composed of a series of 3 questions used to assign patients to one of 5 acuity levels. The ESI triage process relies on experienced nurse judgment to asses patients according to the following questions: (1) Is the patient dying?; (2) Should the patient wait?; and (3) How many resources will this patient require?

Patients dying are categorized to Level 1 (immediate treatment); patients who should not wait are categorized to Level 2 (emergent treatment); patients deemed safe to wait are stratified to levels 3 (urgent treatment) through 5 (non-urgent treatment) by anticipated resource utilization with Level 3 requiring the most resources and Level 5 the least. Thus, the ESI tool stratifies patients based upon nurses' experience and "sixth sense" for immediacy of medical need and resource utilization. Including resource utilization in the determination of triage level, makes the system unique among modern triage systems.

Though currently in widespread use across the US, ESI has several shortcomings. First, ESI has not been adequately validated against outcomes indicating time sensitive or critical care needs. Further, it does not sufficiently distribute patients across the 5 triage levels, resulting in poor discrimination. Almost half of all ED patients nationally are categorized as Level 3, the ambiguous and undifferentiated midpoint of a 5-level system. This results in patients of a wide range of severity clustered in one large group, potentially delaying care to those most ill, countering the objective of triage. Finally, ESI relies heavily on subjective classification and may therefore be limited by inherent variability, inexperience or human error with potential for misclassification.

The electronic triage system reduces this subjectivity, and would improve triage reliability while maintaining validity and ease of use. Therefore, it would be advantageous to provide an automated electronic triage system, based on patient outcomes with improved discrimination.

SUMMARY OF THE INVENTION

The foregoing needs are met, to a great extent, by the present invention, wherein in one aspect a method for emergency department (ED) triage includes assessing individual patients that have presented to the ED, but are waiting for care. The method includes gathering routinely collected demographic and clinical data computing individual risk assessments. Risk estimates are computed for outcomes that include: (1) in-hospital (including ED) mortality, (2) intensive care unit admission, (3) emergent surgical procedure including catheterization, and (4) inpatient hospitalization, (5) other acute clinical outcomes available in electronic medical record.

Additionally, the method includes using this risk assessment to determine a broad care pathway (i.e., stream) in the ED. In accordance with an aspect of the present invention, the method includes using a non-transitory computer readable medium for the execution of steps of the method. The method includes gathering data related to the potential patients comprising age, gender, mode of arrival, blood pressure, heart rate, temperature, respiratory rate, oxygen saturation, complaints, medical/surgical history and chronic conditions. All of these predictor data (or a sub-set) is used to estimate risk for each outcome. The method includes assigning each one of the patients a triage score on a customizable scale (e.g., 1 to 5) based on risk estimates computed for the patient.

In accordance with another aspect of the present invention, the method includes displaying information related to the patient plan. A specific patient score and patient scores for the ED can also be displayed. The method includes alerting the user based on patient risk. Further, the method can include prompting a health care provider for additional information on the patient.

In accordance with still another aspect of the present invention, a system for emergency department (ED) triage a non-transitory computer readable medium programmed for gathering data for patients waiting to be triaged in the ED. The system includes assessing risks for each one of the potential patients waiting in the ED. The system also includes determining a patient plan based on the risk for each one of the potential patients waiting in the ED.

In accordance with another aspect of the present invention, the system includes a computing device selected from a group of a personal computer, laptop, smartphone, tablet, server, and cloud based computing device. Gathering data related to the potential patients includes gathering any of a group of demographics (age and gender), vital signs (temperature, heart rate, systolic blood pressure, respiratory rate, and oxygen saturation), complaint(s), medical/surgical history, chronic conditions, and mode of arrival. The system includes assigning each one of the patients a score indicating the risk to the patient and predicting a patient's needs in the ED at triage. A patient's needs in the ED at triage are predicted using data selected from a group of (1) in-hospital (including ED) mortality, (2) intensive care unit admission, (3) emergent surgical procedure including catheterization, and (4) inpatient hospitalization, (5) other acute clinical outcomes available in electronic medical record. The system includes a display. The display can show a specific patient score as well as a heatmap of patient scores for the ED. The system can be used for alerting the user based on patient risk and prompting a health care provider for additional information on the patient.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention provides a system that uses simple standardized patient information routinely collected at triage to distribute patients amongst triage levels based on parallel outcomes in tandem. The present invention estimates the probability of one or any subset of: (1) in-hospital (including ED) mortality, (2) intensive care unit admission, (3) emergent surgical procedure including catheterization, and (4) inpatient hospitalization, (5) other acute clinical outcomes available in electronic medical record. Risk for each outcome may be estimated in some composite form or individually. In-hospital mortality is defined as death in the ED or in-hospital during the index visit. "Emergent" for emergent procedure is measured within some time within 72 hours of ED disposition. The hospitalization outcome is defined as any admission to an inpatient care sites including ward, intensive care, or direct transfer to an external acute care hospital. Patients transitioned to observation status/care areas were not considered an admission unless their observation ultimately resulted in inpatient hospitalization.

Figure 1:
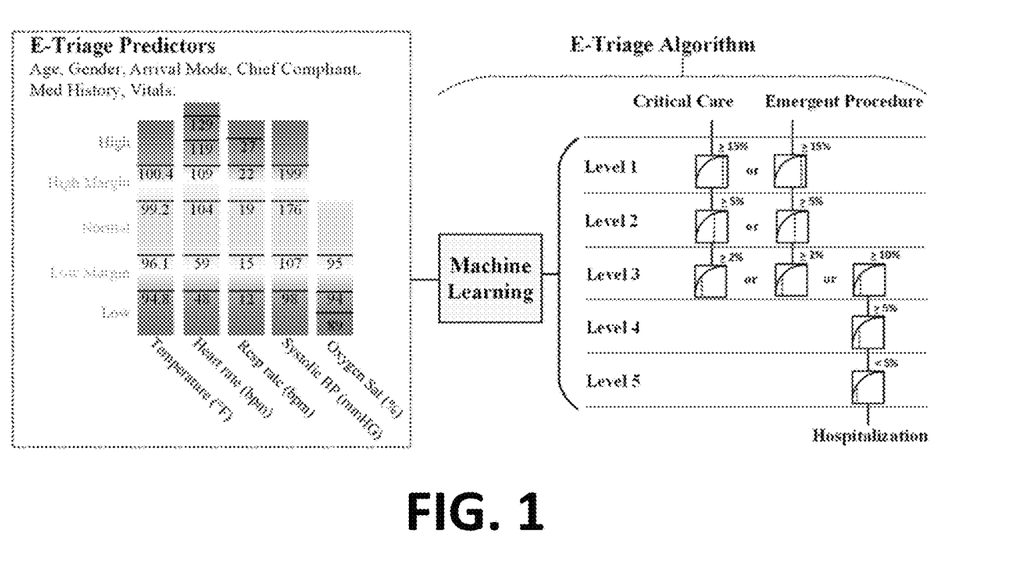
FIG. 1 illustrates e-triage predictors and algorithm with an example emergency department risk profile. The risk profile translates predicted probabilities of outcomes to e-triage levels. Example outcomes are critical care (in-hospital mortality or ICU admission), emergent procedure, and hospital inpatient admission.

Probabilistic predictions of these outcomes are made for patients based upon clinical information routinely collected at triage which include basic demographics (age and gender), vital signs (temperature, heart rate, systolic blood pressure, respiratory rate, and oxygen saturation), complaint(s), medical/surgical history, chronic conditions, and mode of arrival. All of these predictor data (or a sub-set) is used to estimate risk. Vital signs are categorized as normal or gradations of abnormal as seen in FIG. 1. Medical ontologies derived from clinician consensus (modified-Delphi technique) and data from multiple sites have been used to categorize text-based complaints, history, and chronic conditions into clinically meaningful categories. An example of categorization of chief complaints for this may be seen in Table 1 below. Feature selection methods may be applied (or not) to optimize the grouping structure of these text-based predictors to maximize predictive performance with respect to our two outcomes.

TABLE 1

Example map of clinical groupings for EMR-entered chief complaints

| Clinical Groupings | Electronic Medical Record Entered Complaints |
|---|---|
| Abdominal pain | Abdominal pain; Abdominal cramping; Colitis; Constipation; Cramps; Gastroesophageal Reflux; Flank Pain; Gastroparesis |
| Chest pain | Chest pain; Chest tightness; Chest burning; Chest discomfort; Lung pain; Heart problem; |
| Shortness of breath | Shortness of breath; Airway obstruction; Aspiration; Breathing problem; Hyperventilation; Hypoxia; Respiratory Distress |

The present invention, referred to in its various embodiments as E-Triage, herein, was derived using a supervised machine learning prediction engine (FIG. 1) trained from a retrospective cohort of 226,317 ED visits for adults from three separate populations: (1) a nationally representative sample, (2) an urban ED (Johns Hopkins Hospital, Baltimore, MD), and (3) a community ED (Howard County General Hospital, Columbia, MD). ED visit data for 53,591 encounters was collected through the nationally representative National Hospital Ambulatory Care Survey (NHAMCS) conducted by the Center for Disease Control (CDC) between 2008 and 2011. This multi-year sample was collected from between 357 and 373 reporting hospitals each year randomly sampled from a set of 600 eligible hospitals. Patient encounter data for 60,712 and 112,014 visits from the urban and community EDs, respectively, was collected over one year between Aug. 1, 2014 and Oct. 1, 2015 from the electronic medical record (EMR) system at each hospital. Characteristics of these populations may be seen in Table 2.

TABLE 2

Emergency department patient visit outcomes and characteristics

| Population | Urban ED | Community ED | National Sample |
|---|---|---|---|
| Cohort Size (N) | 60,712 | 112,014 | 53,591 |
| Predicted Outcomes (%) | | | |
| Critical Care Outcome | 2.0 | 1.6 | 2.3 |
| In-Hospital Mortality | 0.3 | 0.5 | 0.4 |
| ICU Admission | 1.8 | 1.3 | 2.0 |
| Emergent Surgery Outcome | 1.4 | 1.7 | 0.9 |
| Catheterization | 0.1 | 0.2 | 0.2 |
| Hospitalization (Inpatient) Outcome | 26.0 | 22.3 | 15.9 |
| Secondary Outcomes (%) | | | |
| Elevated Troponin | 2.5 | 1.8 | — |
| Elevated Lactate | 3.6 | 1.2 | — |
| Demographics and Arrival Mode | | | |
| Age: Mean (95% Percentile) | 44 (29-57) | 49 (33-66) | 43 (29-59) |
| Gender: Female (%) | 52.7 | 57.9 | 57.4 |
| Arrival by Ambulance (%) | 20.4 | 25.5 | 18.6 |
| Vital Signs (% Low|% Normal|% High) | | | |
| Temperature | 0.3|97.3|2.4 | 0.2|97.9|1.9 | 0.3|97.5|2.2 |
| Heart Rate | 0.3|89.1|10.5 | 0.5|90.5|9.0 | 0.4|90.4|9.3 |
| Respiratory Rate | 0.4|97.0|2.5 | 1.2|96.0|2.9 | 1.3|92.8|6.0 |
| Systolic Blood Pressure | 2.4|95.2|2.4 | 3.7|95.3|1.0 | 3.0|95.5|1.5 |
| Oxygen Saturation | 3.2|96.8|— | 5.9|94.1|— | 6.6|93.4|— |
| Chief Complaint Sample (%) | | | |
| Abdominal Pain | 11.6 | 14.6 | 11.0 |
| Chest Pain | 7.8 | 9.3 | 7.3 |

TABLE 2-continued

Emergency department patient visit outcomes and characteristics

| Population | Urban ED | Community ED | National Sample |
|---|---|---|---|
| Shortness of Breath | 5.9 | 5.8 | 5.1 |
| Back Pain | 3.1 | 3.3 | 5.0 |
| Headache | 3.1 | 2.8 | 4.0 |
| Active Chronic Problems Sample (%) | | | |
| Diabetes | 8.4 | 3.6 | |
| Coronary Artery Disease (CAD) | 4.0 | 2.0 | — |
| Congestive Heart Failure (CHF) | 3.3 | 1.8 | — |
| Atrial Fibrillation (AFib) | 2.3 | 2.1 | — |
| End Stage Renal Disease (ESRD) | 1.7 | 0.8 | — |

E-triage uses routine information collected at triage to distribute adult patients across a customizable scale based on risk of pre-defined EMR collected outcomes. Ensemble learning is used to create random forest decision tree models for each outcome, per population. Thus, separate models are derived for each outcome from the same predictor data, but are applied in tandem to produce probabilities that map to e-triage levels as seen in FIG. 1. For example in FIG. 1, high severity patients with a probability of critical care (ICU or in-hospital mortality)≥15% or emergent procedure ≥15% were assigned to e-triage Level 1 and probabilities between 5% and 15% were assigned to e-triage level 2. Patients with probabilities of critical care between 2% and 5% or emergent procedure between 2% or 5% or hospitalization >10% were assigned Level 3. The remaining patients with <10% probability of hospitalization were then stratified by their probability of admission (i.e., resource intensity surrogate). It is important to note that risk profile (i.e., cut-off thresholds) that define patients grouped to Level 1 through 5 are not static and may be adapted (i.e., customized) to individual EDs objectives for risk stratification, distribution of patients, and resource allocation.

Figure 2:
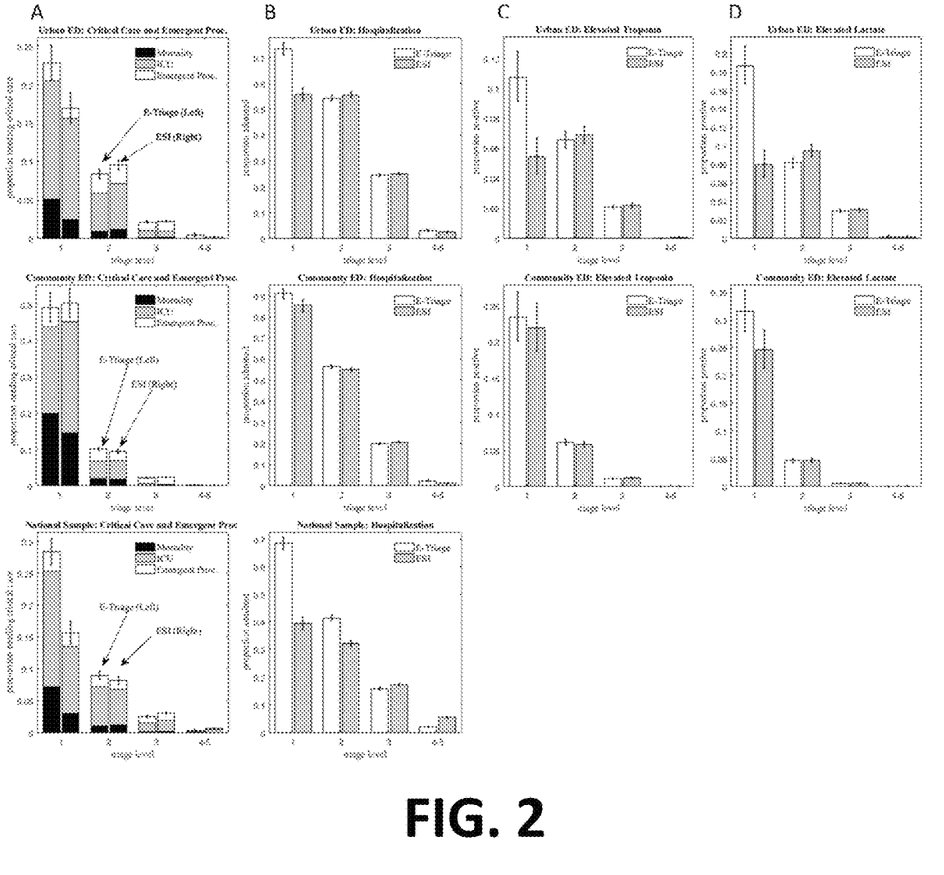
FIG. 2 illustrates graphical views of characteristics of e-triage compared to ESI for e-triage risk profiles derived to distribute patients across triage levels identical to ESI. Characteristics include the proportion with critical care and emergent procedure outcomes (Column A), proportion admitted (B) proportion with elevated troponins (C), and proportion with elevated lactates (D) stratified by triage level for three independent ED populations: (1) a nationally representative sample collected by the Center for Disease Control (CDC) between 2008 and 2011, and a cohort from an (2) urban and (3) community ED between Aug. 1, 2014 and Oct. 1, 2015.

E-triage demonstrated an out-of-sample AUC ranging from 0.86 to 0.92 for the critical care outcome, 0.73 to 0.82 for the emergent procedure outcome, and 0.82 to 0.84 for the hospitalization outcome across ED populations. FIG. 2 illustrates graphical views of characteristics of e-triage compared to ESI on for the three ED populations. FIG. 2 from left-to-right exhibits the proportion of ED visits with predicted and secondary outcomes stratified by triage level. E-triage was able to identify an equal or greater proportion of patients with critical care and emergent procedure outcomes (column A) to Level 1 than the ESI reference standard. The proportion of ED visits with a critical care or emergent procedure outcome in Level 1 patients was: 22.9% e-triage versus 16.9% ESI (difference 6.0%, 95% CI 3.0%, 8.9%) in the urban ED; 49.1% e-triage versus 50.5% ESI (difference −1.4%, CI −6.9%, 4.2%) in the community ED, and; 26.4% e-triage versus 14.7% ESI (difference 11.7%, 95% CI 8.4%, 14.9%) in the national sample. E-triage detection was slightly, but not meaningfully, decreased for the community ED where less than 1% of the total population is triaged to Level 1. Comparative results are displayed for the hospitalization outcome (FIG. 2; column B). E-triage's ability to detect secondary clinical outcomes was similarly equal or greater than the ESI reference standard (FIG. 3; column C and D) at both study sites. The most substantial difference was for Level 1 patients in the urban ED where overall prevalence of elevated troponin (>0.6 ng/ML) and lactate (>2.4 mmol/L) was higher than the community ED.

Significant reclassification of patient visits occurred (e.g., patient with ESI Level 3 and e-triage Level 2) despite evaluating e-triage to match the distribution of patients across triage levels observed by ESI. Much of this reclassification was exhibited in the large majority of ESI Level 3 patients as seen in Table 2. The rate of agreement for ESI Level 3 patients was lower for the national sample (56.2%) compared to the urban (76.6%), and community (74.7%) EDs. Substantial differences in outcome rates between patients in agreement, under-triaged, or over-triaged highlight the opportunity for improved outcomes-based patient differentiation. Compared to patients where Level 3 was in agreement for e-triage and ESI, under-triaged patients were at least 5 times more likely to experience the critical care outcome or emergent surgery outcome, 2 times likely to be admitted to the hospital, and over 2 times more likely to yield elevated troponin or lactate (Table 3) levels. A more substantial inverse trend may be seen for those over-triaged patients.

The E-triage Level is issued immediately at triage and is required to direct future care. 4. Uses a computer to generate decision support. E-triage uses IT to apply it's algorithm to patients and display results. E-triage meets these criteria for successful clinical decision support and provider-IT interactions at triage. Technical details of software and interface development follow.

Figure 3:
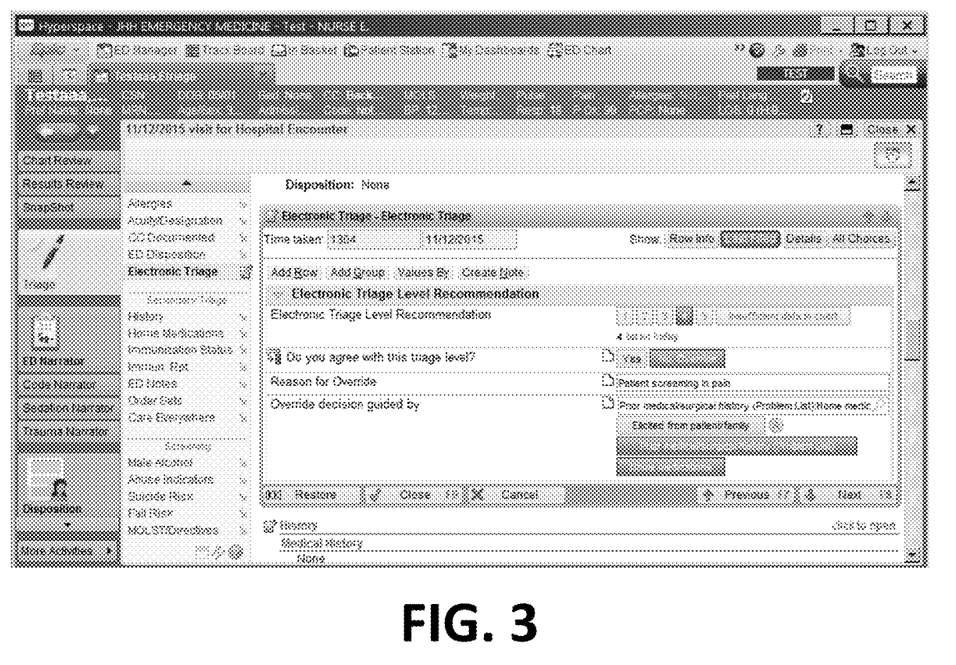
FIG. 3 illustrates an exemplary E-triage Epic Interface.

The application (interface, algorithm engine, and database) has been deployed in two separate ways: (1) embedded into existing Hospital Information Systems (Epic) and (2) as a free-standing, public-facing web application. Programming for each deployment strategy requires the same foundation and will overlap substantially. However, the embedded application must be integrated into Epic. At triage, routine clinical information is entered into Epic's ED Information System (ASAP). Next the user views (i.e., one-click) the E-triage application interface for that specific patient, as illustrated in FIG. 3. This process will ensure no duplicate data entry and seamless integration into workflow. In addition, the application will store triage process time-stamps to support evaluation. This specifically includes the time when ASAP was opened for a patient at triage (triage start) and the

TABLE 3

Outcomes for reclassified Emergency Severity Index Level 3 patients (majority group).

| Population | Re-class | N | Predicted Outcomes | | | Secondary Outcomes | |
|---|---|---|---|---|---|---|---|
| | | | Critical Care | Emergent Procedure | Hospital-ization | Elevated Troponin | Elevated Lactate |
| Urban ED | Agree[1] | 31,456 (76.6%) | 0.7% | 1.2% | 24.6% | 2.0% | 3.0% |
| | Under-Triage[2] | 4,823 (11.7%) | 3.5% | 3.0% | 47.7% | 5.6% | 6.6% |
| | Over-Triage[3] | 4,768 (11.6%) | 0.0% | 0.8% | 5.3% | 0.0% | 0.3% |
| Community ED | Agree[1] | 55,383 (74.7%) | 0.3% | 1.7% | 19.4% | 1.0% | 0.4% |
| | Under-Triage[2] | 9,503 (12.8%) | 2.2% | 4.2% | 44.3% | 3.6% | 2.1% |
| | Over-Triage[3] | 9,224 (12.5%) | 0.0% | 0.2% | 3.8% | 0.1% | 0.0% |
| National Sample | Agree[1] | 14,443 (56.2%) | 1.4% | 1.3% | 17.6% | — | — |
| | Under-Triage[2] | 4,150 (16.1%) | 7.1% | 2.1% | 45.2% | — | — |
| | Over-Triage[3] | 7,123 (27.7%) | 0.2% | 0.2% | 3.7% | — | — |

Definitions:
[1] Agree occurred when a patient's e-triage and ESI levels were equivalent
[2] Under-triage occurred when e-triage estimated a patient higher-risk than ESI (i.e., e-triage < ESI)
[3] Over-triage occurred when e-triaged estimated a patient to be lower risk than ESI (i.e., e-triage > ESI)

Development of the e-triage application will benefit from knowledge gained by prior published efforts to create and apply clinical decision support. In fact, a systematic review of 70 clinical decision support systems in practice found 4 critical features (amongst 15 evaluated) most associated with likelihood of improving clinical care: 1. Provision of decision support as part of workflow. The e-triage application performs triage which is a required initial step for all patients that enter the ED. E-triage relies on the exact same data entry that currently exists in most EDs across the US making it a natural fit into current workflow. 2. Provision of recommendations rather than assessments. E-triage produces a triage level that is directly actionable. Triage levels are used to prioritize patients and in many EDs (including Johns Hopkins) direct patients down pathways where resource intensity and care processes differ. Provision of decision support at the time and location of decision making.

time a final E-triage Level is issued (triage end). Alternatively, the free-standing web application will not require interoperability.

The E-triage interface will evolve and has been designed by triage nurse users. The current Epic-embedded version is in FIG. 3. Data entered into Epic at triage will be automatically communicated to the E-triage application. These fields and layout mimic the currently existing triage interface. It's important to note the 3 questions below the "Electronic Triage Level Recommendation" highlight requirements to maintain some nurse judgment by including an override feature. The frequency, type (i.e., under-triage or over-triage) and reasons for override will be collected by the application and explicitly analyzed to improve E-triage iteratively. A display according to the present invention shows a triage level for a patient in question. However, it can also transform the triage level data for a number of patients waiting in the ED into a visual representation of patients and priority, for example as a heatmap of patients waiting for care. The present invention can also display alerts regarding specific patients or for the ED as a whole. These alerts need not be prescheduled and can be disseminated over a wide range of devices.

Other interface features of note include drop-down menus for chief complaint and medical history fields (i.e., not free text), form-logic for demographic and vital sign fields, and a population selection function (top right corner) available only in the web-based version. Web-based users outside of Johns Hopkins will be able to select "Urban", "Community" or "National" corresponding to the E-triage algorithm developed for each population, respectively. This will allow outside users to explore differences in these populations or select the population that is most relevant to their application.

These steps can be carried out using a non-transitory computer readable medium loaded onto a computing device such as a personal computer, tablet, phablet, smartphone, computer server, cloud based computing device, or any other computing device known to or conceivable by one of skill in the art. Indeed, any suitable hardware and software known to or conceivable by one of skill in the art could be used. It should also be noted that while specific equations are detailed herein, variations on these equations can also be derived, and this application includes any such equation known to or conceivable by one of skill in the art.

A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention.

The computing device should include a display and a user input. This setup allows for the user to change parameters for location, department, patient criteria, etc. This setup also allows for the update of the visual feedback as parameters are changed. It is also possible that the display shows predictions of various ED capacity outcomes. The computing device can also be networked with or otherwise in communication with electrical medical records systems and software. In some embodiments the computing device can be configured to communicate directly via wire or wirelessly with hospital computers, databases, or other systems.

The many features and advantages of the invention are apparent from the detailed specification, and thus, it is intended by the appended claims to cover all such features and advantages of the invention which fall within the true spirit and scope of the invention. Further, because numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A method for performing a triage, the method comprising:
   receiving, by a computing device having a trained machine learning prediction engine, data pertaining to an individual visiting an emergency department, the data pertaining to the individual including health-related information of the individual, wherein:
   the trained machine learning prediction engine having been trained using supervised machine learning and training data related to a plurality of emergency department visits by individuals of an emergency department population, and
   the trained machine learning prediction engine having used ensemble learning to create separate decision forest models, each of which being for prediction of a respective outcome of a plurality of predefined future acute clinical outcomes for the individuals of the emergency department population;
   applying, in tandem by the computing device, the data pertaining to the individual to the separate decision forest models for prediction of the respective outcomes of the plurality of future acute clinical outcomes for the individual of the emergency department population to produce predicted probabilities of a risk for each of the respective outcomes for the individual of the emergency department population;
   mapping, by the computing device, one of the produced predicted probabilities of the risk for the respective outcomes to one of a plurality of triage levels, the one of the plurality of triage levels being required to direct care for the individual in accordance with the one of the plurality of triage levels, the one of the produced predicted probabilities being mapped is based on values of the produced predicted probabilities;
   making available, by the computing device, information regarding the one of the plurality of triage levels;
   providing, by the computing device, an override feature to allow a health care provider to override the one of the plurality of triage levels;
   collecting, by the computing device, a frequency of an override, a type of the override, and optionally reasons for the override; and
   analyzing, by the computing device, the collected frequency of the override, the type of the override, and optionally the reasons for the override to iteratively improve an accuracy of the mapping of the one of the produced predicted probabilities of the risk for the respective outcomes to the one of the plurality of triage levels.

2. The method of claim 1, wherein the health-related information of the individual comprises information of a group of one or more of demographic information, vital sign information, body temperature, heart rate, systolic blood pressure, respiratory rate, oxygen saturation, complaint information, medical history, information related to any chronic conditions, and mode of arrival.

3. The method of claim 1, further comprising:
   assigning, by the computing device, a triage level to the individual based on the predicted probabilities of the risk for the each future acute clinical outcome.

4. The method of claim 3, further comprising:
   displaying, by the computing device, a visual representation of the risk for future acute clinical outcomes associated with one or more of the individuals visiting the emergency department.

5. The method of claim 1, wherein the plurality of predefined future acute clinical outcomes for the emergency department population include in-hospital mortality, intensive care unit admission, an emergent surgical procedure within a given time period of emergency department disposition, and inpatient hospitalization.

6. The method of claim 1, further comprising:
prompting a health care provider for information.

7. The method of claim 1, wherein the computing device communicates bidirectionally with an electronic medical records system.

8. At least one non-transitory computer readable medium having instructions stored thereon, which when executed by a computing device configure the computing device to:
receive data pertaining to an individual visiting an emergency department, the data pertaining to the individual including health-related information of the individual, wherein:
a trained machine learning prediction engine of the computing device having been trained using supervised machine learning and training data related to a plurality of emergency department visits by individuals of an emergency department population, and
the trained machine learning prediction engine having used ensemble learning to create separate decision forest models, each of which being for prediction of a respective outcome of a plurality of predefined future acute clinical outcomes for the individuals of the emergency department population;
apply, in tandem, the data pertaining to the individual to the separate decision forest models for prediction of the respective outcomes of the plurality of future acute clinical outcomes for the individual of the emergency department population to produce predicted probabilities of a risk for each of the respective outcomes for the individual of the emergency department population;
map one of the produced predicted probabilities of the risk for the respective outcomes to one of a plurality of triage levels, the one of the plurality of triage levels being required to direct care for the individual in accordance with the one of the plurality of triage levels, the one of the produced predicted probabilities being mapped is based on values of the produced predicted probabilities;
make available information regarding the one of the plurality of triage levels;
provide an override feature to allow a health care provider to override the one of the plurality of triage levels;
collect a frequency of an override, a type of the override, and optionally reasons for the override; and
analyze the collected frequency of the override, the type of the override, and optionally the reasons for the override to iteratively improve an accuracy of the mapping of the one of the produced predicted probabilities of the risk for the respective outcomes to the one of the plurality of triage levels.

9. The at least one non-transitory computer readable medium of claim 8, wherein the health-related information of the individual comprises information of a group of one or more of demographic information, vital sign information, body temperature, heart rate, systolic blood pressure, respiratory rate, oxygen saturation, complaint information, medical history, information related to any chronic conditions, and mode of arrival.

10. The at least one non-transitory computer readable medium of claim 8, wherein the instructions further configure the computing device to:
assign a triage level to the individual based on the predicted probabilities of the risk for the each future acute clinical outcome.

11. The at least one computer readable medium of claim 10, wherein the instructions further configure the computing device to:
display a visual representation of the risk for future acute clinical outcomes associated with one or more individuals visiting the emergency department.

12. The at least one computer readable medium of claim 8, wherein the plurality of predefined future acute clinical outcomes for the emergency department population include in-hospital mortality, intensive care unit admission, an emergent surgical procedure within a given time period of emergency department disposition, and inpatient hospitalization.

13. The at least one computer readable medium of claim 8, wherein the instructions further configure the computing device to provide a graphical user interface that allows a health care provider to override the mapped one of the plurality of triage levels for the individual.

14. A computing system for performing a triage, the computing system comprising:
at least one non-transitory computer readable medium having instructions recorded thereon, which when executed by the computing system configure the computing system to:
receive data pertaining to an individual visiting an emergency department, the data pertaining to the individual including health-related information of the individual, wherein:
a trained machine learning prediction engine of the computing system having been trained using supervised machine learning and training data related to a plurality of emergency department visits by individuals of an emergency department population, and
the trained machine learning prediction engine having used ensemble learning to create separate decision forest models, each of which being for prediction of a respective outcome of a plurality of predefined future acute clinical outcomes for the individuals of the emergency department population;
apply, in tandem, the data pertaining to the individual to the separate decision forest models for prediction of the respective outcomes of the plurality of future acute clinical outcomes for the individual of the emergency department population to produce predicted probabilities of a risk for each of the respective outcomes for the individual of the emergency department population;
map one of the produced predicted probabilities of the risk for the respective outcomes to one of a plurality of triage levels, the one of the plurality of triage levels being required to direct care for the individual in accordance with the one of the plurality of triage levels, the one of the produced predicted probabilities being mapped is based on values of the produced predicted probabilities;
make available information regarding the one of the plurality of triage levels;
provide an override feature to allow a health care provider to override the one of the plurality of triage levels;
collect a frequency of an override, a type of the override, and optionally reasons for the override; and
analyze the collected frequency of the override, the type of the override, and optionally the reasons for the override to iteratively improve an accuracy of the mapping of the one of the produced predicted probabilities of the risk for the respective outcomes to the one of the plurality of triage levels.

15. The computing system of claim 14, wherein the health-related information of the individual comprises information of a group of one or more of demographic information, vital sign information, body temperature, heart rate, systolic blood pressure, respiratory rate, oxygen saturation, complaint information, medical history, information related to any chronic conditions, and mode of arrival.

16. The computing system of claim 14, wherein the computing system is further configured to:
assign a triage level to the individual based on the produced predicted probabilities, the triage level being indicative of a medical risk to the individual; and
display a visual representation of the risk for future acute clinical outcomes associated with one or more of the individuals visiting the emergency department.

17. The computing system of claim 14, wherein the plurality of predefined future acute clinical outcomes for the emergency department population include in-hospital mortality, intensive care unit admission, an emergent surgical procedure within a given time period of emergency department disposition, and inpatient hospitalization.

18. The computing system of claim 14, wherein the computing system is further configured to provide a graphical user interface that allows a health care provider to override the mapped one of the plurality of triage levels for the individual.

19. The computing system of claim 18, wherein the graphical user interface further allows the health care provider to provide a reason for the override for use in improving accuracy of the mapped one of the plurality of triage levels for the emergency department population.

20. The computing system of claim 18, wherein the computing system is further configured to communicate with at least one other computing system.

21. The method of claim 1, further comprising:
alerting, by the computing device, a user based on patient risk.

22. The method of claim 1, wherein:
the receiving further comprises receiving a selection of one of a plurality of separate emergency department populations,
the trained machine learning prediction engine having been trained using training data related to a plurality of emergency department visits by individuals of the plurality of separate emergency department populations, each of the plurality of separate emergency department populations representing a respective emergency department population based on a type of community in which the emergency department is located,
the trained machine learning prediction engine having used ensemble learning to create decision forest models for prediction of a plurality of predefined future acute clinical outcomes for individuals of each of the plurality of separate emergency department populations, and
the applying further comprising applying, in tandem by the computing device, the data pertaining to the individual to the decision forest models for prediction of each future acute clinical outcome for the individual of the selected one of the plurality of separate emergency department populations to produce predicted probabilities of a risk for the each future clinical outcome for the individual of the selected one of the plurality of separate emergency department populations.

23. A computing system for performing a triage, the computing system comprising:
at least one non-transitory computer readable medium having instructions recorded thereon to configure the computing system to perform operations comprising:
training a machine learning prediction engine using supervised machine learning and training data related to a plurality of emergency department visits by individuals of an emergency department population, the machine learning prediction engine using ensemble learning to create separate decision forest models, each of which being for prediction of a respective outcome of a plurality of predefined future acute clinical outcomes for the individuals of the emergency department population;
receiving, after the training of the machine learning prediction engine, data pertaining to an individual visiting an emergency department, the data pertaining to the individual including health-related information of the individual;
applying, in tandem, the data pertaining to the individual to the separate decision forest models for prediction of the respective outcomes of the plurality of future clinical outcomes for the individual of the emergency department population to produce predicted probabilities of a risk for each of the respective outcomes for the individual of the emergency department population;
mapping one of the produced predicted probabilities of the risk for the respective outcomes to one of a plurality of triage levels, the one of the plurality of triage levels being required to direct care for the individual in accordance with the one of the plurality of triage levels, the one of the produced predicted probabilities being mapped is based on values of the produced predicted probabilities;
making available information regarding the one of the plurality of triage levels for displaying;
providing an override feature to allow a health care provider to override the one of the plurality of triage levels;
collecting a frequency of an override, a type of the override, and optionally reasons for the override; and
analyzing the collected frequency of the override, the type of the override, and optionally the reasons for the override to iteratively improve an accuracy of the mapping of the one of the produced predicted probabilities of the risk for the respective outcomes to the one of the plurality of triage levels.

24. The computing system of claim 23, wherein:
the receiving further comprises receiving a selection of one of a plurality of separate emergency department populations,
the trained machine learning prediction engine having been trained using training data related to a plurality of emergency department visits by individuals of a plurality of separate emergency department populations, each of the plurality of separate emergency department populations representing a respective emergency department population based on a type of community in which the emergency department is located,
the trained machine learning prediction engine having used ensemble learning to create decision forest models for prediction of a plurality of predefined future acute clinical outcomes for individuals of each of the plurality of separate emergency department populations, and
the applying further comprising applying, in tandem by the computing device, the data pertaining to the individual to the decision forest models for prediction of each future acute clinical outcome for the individual of the selected one of the plurality of separate emergency department populations to produce predicted probabilities of a risk for the each future clinical outcome for the individual of the selected one of the plurality of separate emergency department populations.

\* \* \* \* \*